(12) United States Patent
Washburn et al.

(10) Patent No.: US 7,052,459 B2
(45) Date of Patent: May 30, 2006

(54) METHOD AND APPARATUS FOR CONTROLLING ULTRASOUND SYSTEMS

(75) Inventors: Michael Joseph Washburn, Brookfield, WI (US); Brooks Matthew Hawley, Milwaukee, WI (US); Scot David Prichard, Muskego, WI (US)

(73) Assignee: General Electric Company, Schenectady, NY (US)

( * ) Notice: Subject to any disclaimer, the term of this patent is extended or adjusted under 35 U.S.C. 154(b) by 228 days.

(21) Appl. No.: 10/659,143

(22) Filed: Sep. 10, 2003

(65) Prior Publication Data

US 2005/0054920 A1   Mar. 10, 2005

(51) Int. Cl.
*A61B 8/00* (2006.01)

(52) U.S. Cl. .................................... 600/437

(58) Field of Classification Search ......... 600/437–471
See application file for complete search history.

(56) References Cited

U.S. PATENT DOCUMENTS

| | | | | |
|---|---|---|---|---|
| 5,161,535 A | * | 11/1992 | Short et al. ................. | 600/437 |
| 5,315,999 A | * | 5/1994 | Kinicki et al. .............. | 600/443 |
| 5,544,654 A | * | 8/1996 | Murphy et al. ............. | 600/443 |
| 5,553,620 A | * | 9/1996 | Snider et al. ............... | 600/440 |
| 5,774,841 A | | 6/1998 | Salazar et al. | |
| 5,853,367 A | * | 12/1998 | Chalek et al. .............. | 600/437 |
| 5,868,676 A | * | 2/1999 | McCabe et al. ............ | 600/454 |
| 5,970,457 A | | 10/1999 | Brant et al. | |
| 6,063,030 A | * | 5/2000 | Vara et al. .................. | 600/437 |
| 6,278,975 B1 | | 8/2001 | Brant et al. | |
| 6,468,212 B1 | * | 10/2002 | Scott et al. ................. | 600/437 |
| 6,485,421 B1 | * | 11/2002 | Uehara ....................... | 600/437 |
| 6,514,201 B1 | | 2/2003 | Greenberg | |
| 6,674,879 B1 | * | 1/2004 | Weisman et al. ........... | 382/128 |
| 6,760,890 B1 | * | 7/2004 | Makinen ....................... | 716/4 |
| 6,773,398 B1 | * | 8/2004 | Ogasawara et al. ......... | 600/437 |

* cited by examiner

*Primary Examiner*—Francis J. Jaworski
(74) *Attorney, Agent, or Firm*—Carl B. Horton, Esq.; Armstrong Teasdale LLP

(57) ABSTRACT

A method and system providing control of an ultrasound system with a user interface is provided. The user interface for controlling the ultrasound system includes a plurality of selectable elements for controlling operation of the ultrasound system and a plurality of identifiers. Each identifier corresponds to one of the plurality of selectable elements and associates control commands with the selectable elements.

23 Claims, 6 Drawing Sheets

METHOD AND APPARATUS FOR CONTROLLING ULTRASOUND SYSTEMS

BACKGROUND OF THE INVENTION

This invention relates generally to ultrasound systems and, more particularly, to methods and devices for controlling ultrasound systems.

In many typical ultrasound systems having, for example, an ultrasound machine or scanner, a large set of controls is provided for use by a user to control the ultrasound system. These controls may be used to drive the operation and/or behavior of the ultrasound machine. Because the physical space on the ultrasound machine is limited, it is often not possible to provide (e.g., expose) all controls at all times. Thus, a user is not able to access all controls at a single time.

A common way to handle the limited space for controls is to use an input device, such as a touch panel having on-screen controls, or other generic input device. The content of the generic input device, such as, for example, the specific control functions displayed, typically varies depending on the context of the ultrasound machine (e.g., based upon the particular operation to be performed). Therefore, only the necessary controls for the particular mode of operation are available for access by a user at any given time.

Additionally, voice commands may be used to operate an ultrasound system. However, again, because of the large set of controls, if each control is given a unique voice command, a very large command set can result. This large command set may reduce the accuracy of the voice recognition system, slow the speed of command recognition, cause misinterpreted commands due to the similarity of many of the commands and/or make it difficult for the user to learn the full list of commands. Further, if the user creates control functions once the ultrasound machine is installed, then it is difficult to provide a way to drive these control functions by voice commands.

BRIEF DESCRIPTION OF THE INVENTION

In one embodiment, a user interface for controlling an ultrasound system is provided. The user interface includes a plurality of selectable elements for controlling operation of the ultrasound system and a plurality of identifiers. Each identifier corresponds to one of the plurality of selectable elements and associates control commands with the selectable elements.

In another embodiment, a method for controlling an ultrasound system is provided. The method includes associating a set of identifiers with a plurality of operations for controlling the ultrasound system, receiving control commands, and performing operations based upon the received control commands corresponding to one or more of the set of identifiers.

DETAILED DESCRIPTION OF THE INVENTION

Exemplary embodiments of ultrasound systems and methods for controlling such systems are described in detail below. A detailed description of exemplary ultrasound systems will first be provided followed by a detailed description of various embodiments of a user input for controlling the operation of ultrasound systems.

Figure 1:
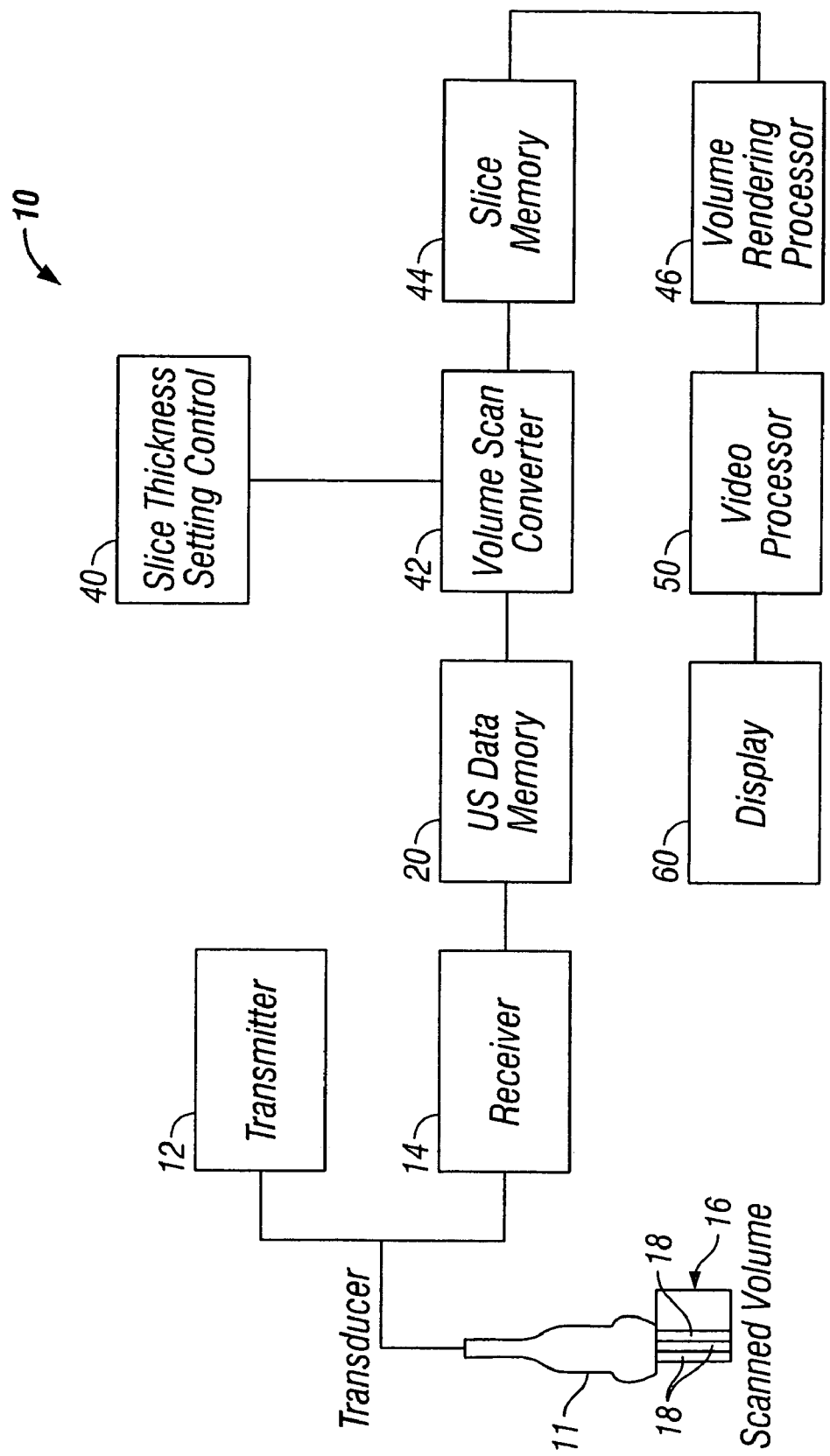
FIG. 1 is a block diagram of an ultrasound system in accordance with one exemplary embodiment of the present invention.

FIG. 1 illustrates a block diagram of an exemplary embodiment of an ultrasound system 10. The ultrasound system 10 includes a probe 11, such as, for example, a transducer, connected to a transmitter 12 and a receiver 14. The probe 11 transmits ultrasonic pulses and receives echoes from structures inside a scanned ultrasound volume 16. A memory 20 stores ultrasound data from the receiver 14 derived from the scanned ultrasound volume 16. The volume 16 may be obtained by various techniques, including, for example, real-time imaging, volume scanning, scanning with transducers having positioning sensors, freehand scanning using a Voxel correlation technique or scanning with matrix array transducers and the like.

The probe 11 is moved, such as along a linear or arcuate path, while scanning a region of interest (ROI). At each linear or arcuate position, the probe 11 obtains scan planes 18. The scan planes 18 are collected for a thickness, such as from a group or set of adjacent scan planes 18. The scan planes 18 are stored in the memory 20, and then passed to a volume scan converter 42. In some embodiments, the probe 11 may obtain lines instead of the scan planes 18, and the memory 20 may store lines obtained by the probe 11 rather than the scan planes 18. The volume scan converter 42 may store lines obtained by the probe 11 rather than the scan planes 18. The volume scan converter 42 receives a slice thickness setting from a slice thickness setting control 40, which identifies the thickness of a slice to be created from the scan planes 18. The volume scan converter 42 creates a data slice from multiple adjacent scan planes 18. The number of adjacent scan planes 18 that are obtained to form each data slice is dependent upon the thickness selected by the slice thickness setting control 40. The data slice is stored in slice memory 44 and is accessed by a volume rendering processor 46. The volume rendering processor 46 performs volume rendering upon the data slice. The output of the volume rendering processor 46 is passed to a video processor 50 and a display 60.

The position of each echo signal sample (Voxel) is defined in terms of geometrical accuracy (i.e., the distance from one Voxel to the next) and ultrasonic response (and derived values from the ultrasonic response). Suitable ultrasonic responses include gray scale values, color flow values, and angio or power Doppler information.

It should be noted that the ultrasound system 10 may include additional or different components. For example, a user interface or input may be provided and used to control the operation of the ultrasound system 10, including, to control the input of patient data, scan parameters, a change of scan mode, and the like.

Figure 2:
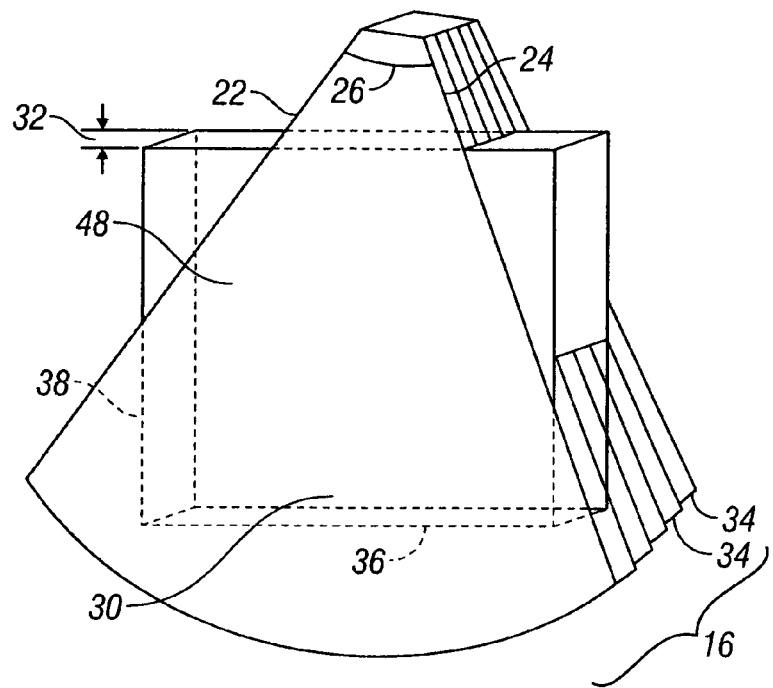
FIG. 2 is a perspective view of a real-time volume acquired by the system of FIG. 1 in accordance with an exemplary embodiment of the present invention.

FIG. 2 illustrates a real-time volume 16 acquired by the ultrasound system 10 of FIG. 1. It should be noted that the ultrasound system 100 of FIG. 3 as described below may also be used to acquire the real-time volume 16. The volume 16 includes a sector shaped cross-section with radial borders 22 and 24 diverging from one another at an angle 26. The probe 11 (shown in FIG. 1) electronically focuses and directs ultrasound firings longitudinally to scan along adjacent scan lines in each scan plane 18 and electronically or mechanically focuses and directs ultrasound firings laterally to scan adjacent scan planes 18. Scan planes 18 obtained by the probe 11, and as illustrated in FIG. 1, are stored in the memory 20 and are scan converted from spherical to Cartesian coordinates by the volume scan converter 42. A volume comprising multiple scan planes is output from the volume scan converter 42 and stored in the slice memory 44 as a rendering box 30. The rendering box 30 in the slice memory 44 is formed from multiple adjacent image planes 34.

The rendering box 30 may be defined in size by an operator using a user interface or input to have a slice thickness 32, width 36 and height 38. The volume scan converter 42 may be controlled by the slice thickness setting control 40 to adjust the thickness parameter of the slice to form a rendering box 30 of the desired thickness. The rendering box 30 designates the portion of the scanned volume 16 that is volume rendered. The volume rendering processor 46 accesses the slice memory 44 and renders along the slice thickness 32 of the rendering box 30.

Referring now to FIGS. 1 and 2, during operation, a slice having a pre-defined, substantially constant thickness (also referred to as the rendering box 30) is acquired by the slice thickness setting control 40 and is processed in the volume scan converter 42. The echo data representing the rendering box 30 may be stored in the slice memory 44. Predefined thicknesses between about 2 mm and about 20 mm are typical, however, thicknesses less than about 2 mm or greater than about 20 mm may also be suitable depending on the application and the size of the area to be scanned. The slice thickness setting control 40 may include a rotatable knob with discrete or continuous thickness settings.

The volume rendering processor 46 projects the rendering box 30 onto an image portion 48 of an image plane 34. Following processing in the volume rendering processor 46, the pixel data in the image portion 48 may pass through a video processor 50 and then to a display 60. The rendering box 30 may be located at any position and oriented at any direction within the scanned volume 16. In some situations, depending on the size of the region being scanned, it may be advantageous for the rendering box 30 to be only a small portion of the scanned volume 16.

Figure 3:
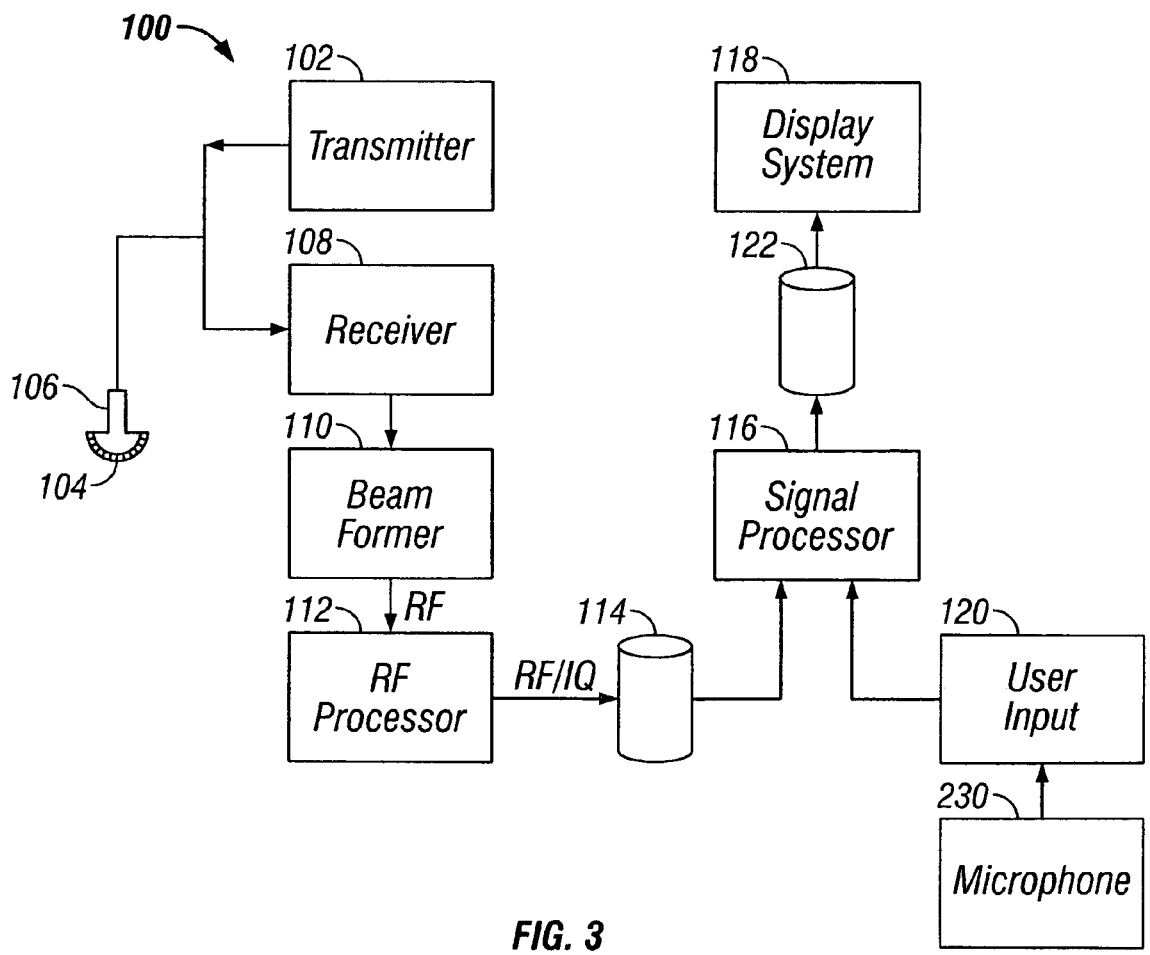
FIG. 3 is an ultrasound system in accordance with another exemplary embodiment of the present invention.

FIG. 3 illustrates a block diagram of another exemplary embodiment of an ultrasound system 100. The ultrasound system 100 includes a transmitter 102 that drives transducers 104 within a probe 106 to emit pulsed ultrasonic signals into a body. A variety of geometries may be used. The ultrasonic signals are back-scattered from structures in the body, like blood cells or muscular tissue, to produce echoes that return to the transducers 104. The echoes are received by a receiver 108. The received echoes are passed through a beamformer 110, which performs beamforming and outputs an RF signal. The RF signal then passes through an RF processor 112. Alternatively, the RF processor 112 may include a complex demodulator (not shown) that demodulates the RF signal to form IQ data pairs representative of the echo signals. The RF or IQ signal data may then be routed directly to an RF/IQ buffer 114 for temporary storage. A user input device 120 as described in more detail below may be used to control operation of the ultrasound system 100, including, to control the input of patient data, scan parameters, a change of scan mode, and the like. This may include using voice commands provided via a microphone 230.

The ultrasound system 100 also includes a signal processor 116 to process the acquired ultrasound information (i.e., RF signal data or IQ data pairs) and prepare frames of ultrasound information for display on display system 118. The signal processor 116 is adapted to perform one or more processing operations according to a plurality of selectable ultrasound modalities on the acquired ultrasound information. Acquired ultrasound information may be processed in real-time during a scanning session as the echo signals are received. Additionally or alternatively, the ultrasound information may be stored temporarily in the RF/IQ buffer 114 during a scanning session and processed in less than real-time in a live or off-line operation.

The ultrasound system 100 may continuously acquire ultrasound information at a frame rate that exceeds fifty frames per second, which is the approximate perception rate of the human eye. The acquired ultrasound information is displayed on the display system 118 at a slower frame-rate. An image buffer 122 is included for storing processed frames of acquired ultrasound information that are not scheduled to be displayed immediately. In an exemplary embodiment, the image buffer 122 is of sufficient capacity to store at least several seconds worth of frames of ultrasound information. The frames of ultrasound information are stored in a manner to facilitate retrieval thereof according to its order or time of acquisition. The image buffer 122 may comprise any known data storage medium.

Referring now to a user interface or input, such as, for example, the user input device 120 (shown in FIG. 3), various embodiments may be implemented for controlling the ultrasound systems 10 and 100. Such various embodiments may include control functionality, such as a set of user controls for controlling the ultrasound systems 10 and 100. The set of user controls may be provided, for example, as part of a touch screen or panel, or as manual inputs, including, for example, user operable switches, buttons, and the like. The set of user controls may be manually operable or voice operated.

Figure 4:
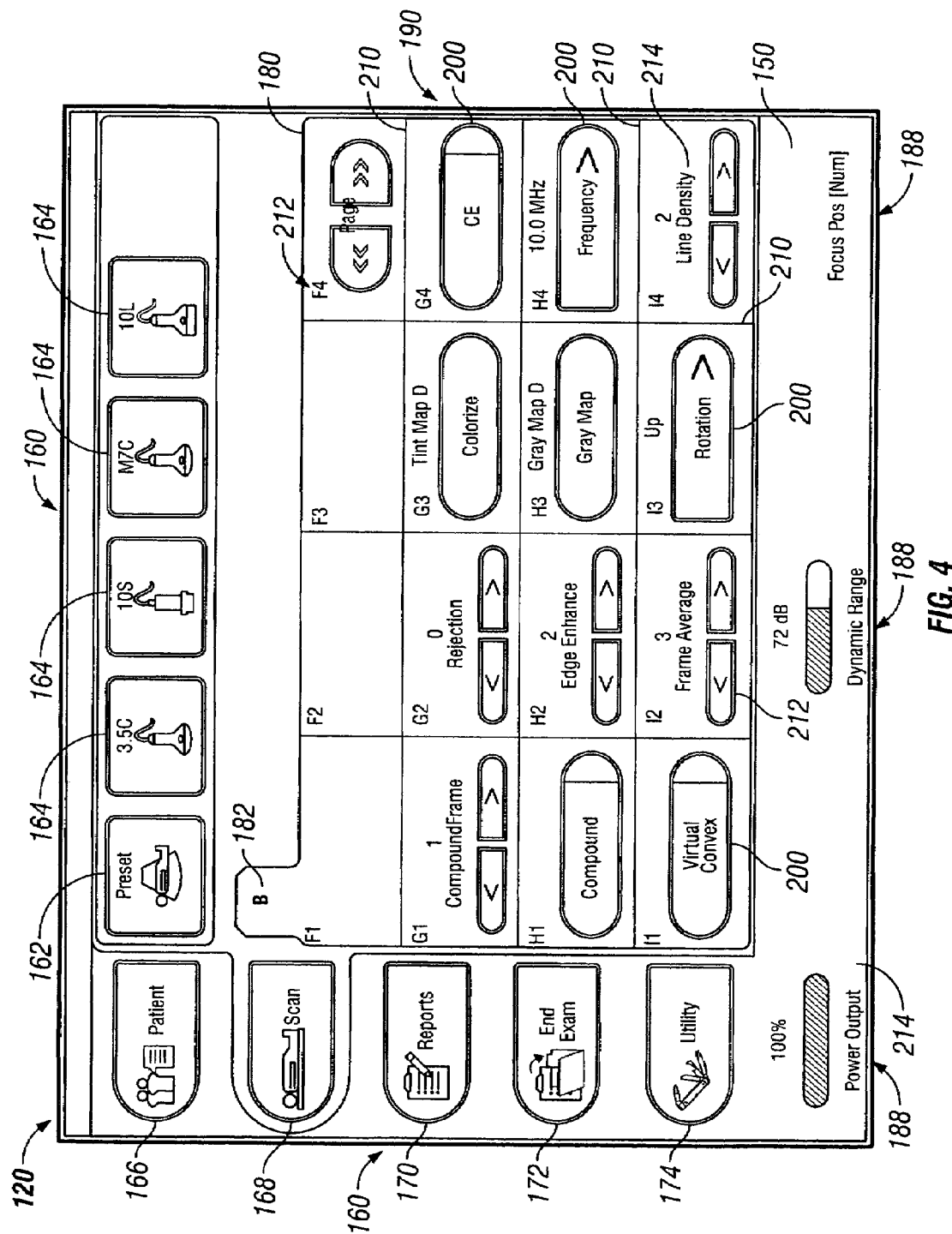
FIG. 4 is a an exemplary embodiment of a user input of an ultrasound system displaying an exemplary control screen.

In an exemplary embodiment as shown in FIG. 4, a user input device 120 may include a user interface, such as, for example, a panel or screen 150, that is operable and selectable by touching the screen 150 to select the desired operation or command for controlling the ultrasound systems 10 and 100. The user input device 120 may also include a voice control input or voice activated component (not shown), such as a microphone 230 (shown in FIG. 3), for controlling the operation of the ultrasound systems 10 and 100.

Specifically, and as shown in FIG. 4, the screen 150 includes a first set of selectable elements 160, for example, a plurality of icons selectable by a user touching the icons on the screen 150 or by voice command as described below, that control operation of the ultrasound systems 10 and 100 in various modes of operation. In one exemplary embodiment, the plurality of selectable elements 160 are fixed and do not change based upon the particular mode of operation. Thus, the icons do not change when the mode of operation changes, for example, as selected by a user. The first set of selectable elements 160 may include, for example, functionality to control general operation of the ultrasound systems 10 and 100. The icons, may control, for example, the area of a patient to scan (Preset icon 162) and/or the selection of a particular transducer to use for a scan (3.5C, 10S, M7C and 10L icons 164). The icons may also allow for selection of general operations such as to enter patient information (Patient icon 166), start a scan (Scan icon 168), create or generate a report (Reports icon 170), end a scan or exam (End Exam icon 172) and/or configure the ultrasound machines 10 and 100 (Utility icon 174). These icons are selectable by touching the screen 150 or by voice commands as described below.

The screen 150 also includes a control portion 180 having a second set of selectable elements 190, for example, a plurality of icons 200 selectable by a user touching the icons 200 on the screen 150 or by voice command as described below, that control operation of the ultrasound systems 10 and 100 in various modes of operation. In one exemplary embodiment, the plurality of selectable elements 190 change based upon the selected mode of operation. Thus, the icons 200 change when the mode of operation changes, for example, as selected by a user. A mode selection element, such as a tab 182, indicates the current mode of operation and defines a set of icons 200 corresponding to that mode of operation to be displayed in the control portion 180. The second set of selectable elements 190 may include, for example, functionality to control operation of the ultrasound systems 10 and 100 in the selected mode of operation. The icons 200 may control, for example, the parameters of operation during the selected mode of operation. For example, and as shown in FIG. 4, when a B-mode of operation is selected, the icons 200, may control, for example, the scanning parameters in the B-mode, such as compounding, rotation, map, frequency, etc. These icons 200 are selectable by touching the screen 150 or by voice commands as described below.

Figure 5:
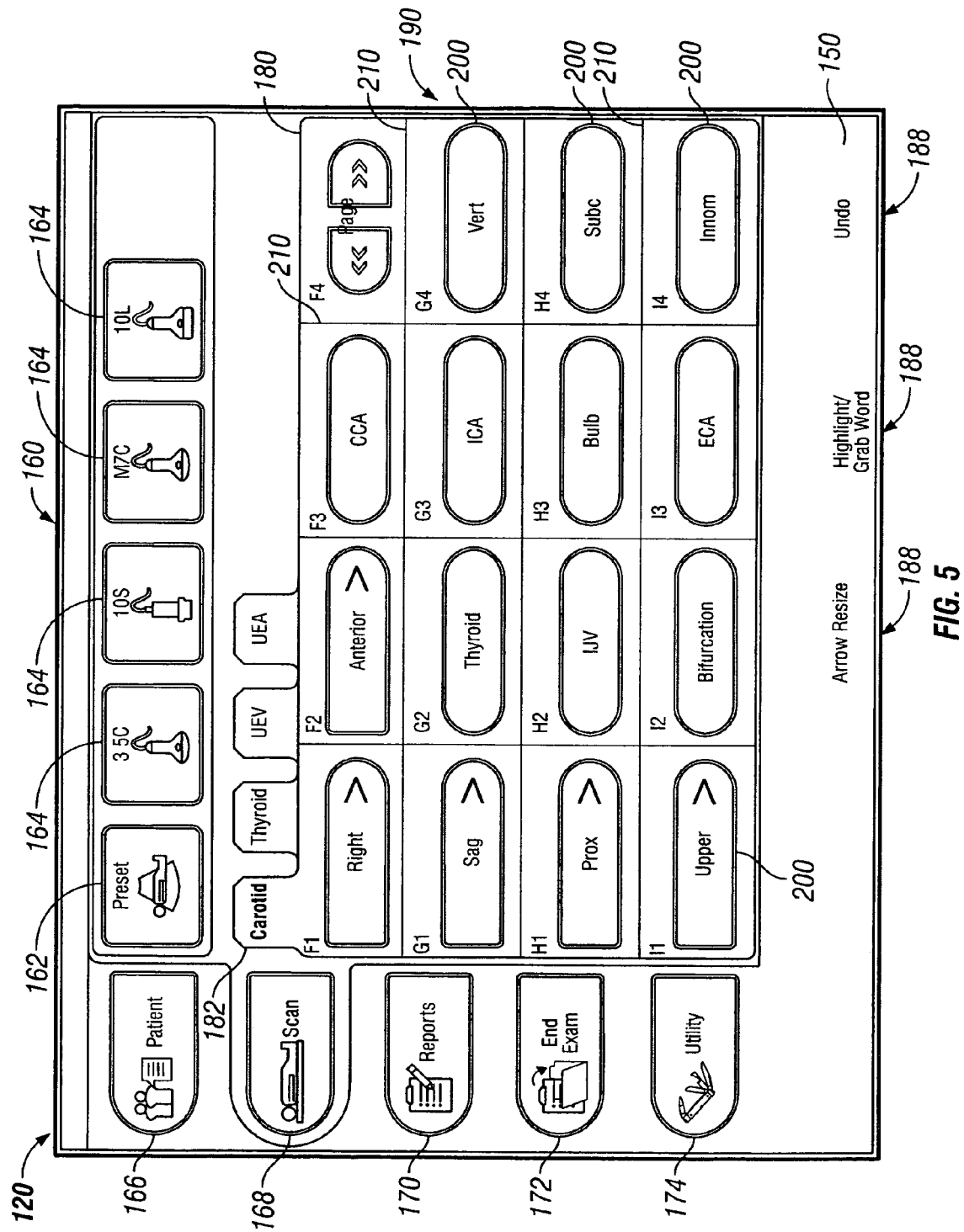
FIG. 5 is the user input of FIG. 4 displaying another exemplary control screen.

It should be noted that the number and type of icons 200 change based upon the mode of operation selected. For example, as shown in FIG. 5, the icons 200 in the control portion 180 correspond to control functionally desired or needed during a Carotid mode of operation, with the mode of operation selected and indicated by the tab 182. More than one tab 182 may be displayed on the screen 150 that are selectable by a user to change the mode of operation, thereby changing the icons 200 displayed within the control portion 180. For example, in addition to the Carotid tab 182, tabs 184 for other modes of operation, such as, Thyroid, UEV and UEA may be provided. The tabs 182 and 184 may be selected by a user or predetermined based upon a particular procedure to be performed. Thus, the tabs 182 and 184 are selectable based upon the mode of operation.

A set of indicators 188 are also provided on the screen 150 that correspond to physical controls (not shown) of the ultrasound systems 10 and 100. The set of indicators 188 also change based upon the mode of operation and may, for example, indicate the level of a particular setting selectable by a physical rotary control (e.g., dynamic range as shown in FIG. 4), or the option selectable by a physical button (e.g., Undo as shown in FIG. 5). In an exemplary embodiment, each of the indicators 188 is displayed on the screen in proximity to (e.g., above) its corresponding physical control provided as part of the ultrasound systems 10 and 100.

In an exemplary embodiment, the control portion 180 is configured as a matrix or grid defined by grid lines 210. The matrix or grid defines locations for each of the icons 200. Specifically, an identifier 212 is associated with each grid position or cell 214 having a corresponding icon 200 therein. In an exemplary embodiment, the identifier associates a voice command with a control command represented by the icon 200 for controlling an operation or parameter of the ultrasound systems 10 and 100. The identifier 212 does not change when the mode of operation changes. As described above, the icons 200 displayed in the control portion 180 may change with a change in the mode of operation. Thus, in different modes of operation, particular identifiers 212 correspond to different icons 200 for controlling a different operation or parameter during that mode of operation. It should be noted that some of the cells 214 may not include a corresponding icon 200 in a particular mode of operation.

In an exemplary embodiment, an icon is selectable by a user by touching the icon displayed on the screen 150 or by voice command. Specifically, during a particular mode of operation, a user may touch the icon 200 to select or adjust a particular parameter in that mode of operation. The various parameters or controls represented by the icons also may be selected using voice commands. In an exemplary embodiment, a user, using a voice control input, such as, for example, a microphone 230 (shown in FIG. 3) that may be wireless or hardwired to the user input 120, may control with voice commands the operation of the ultrasound systems 10 and 100. Specifically, the icons 200 may be selected using the identifier 212 associated with a particular desired or required operation or parameter. For example, the user may speak into the microphone 230 the identifier(s) 212 associated with the icon(s) 200 representing the desired or required operation or parameter, which may include a desired or required change. For example, a user may speak "G1 down," which would decrement the parameter associated with the icon in the cell 214 associated with the G1 identifier 212. Thus, a user can control the ultrasound systems 10 and 100 with a simple set of voice commands defined by the identifiers 212.

It should be noted that voice commands also may be provided using word commands for operations or parameters that are often used (i.e., high use controls). For example, a user may speak "scan" to activate the scan operation associated with the Scan icon 168. The word commands may also be used in connection with high use controls in the control portion 180. Further, as should be appreciated, the voice control operation and display of icons on the screen 150 may be provided in various different manners based upon the requirements of the specific ultrasound system.

Figures 6, 7:
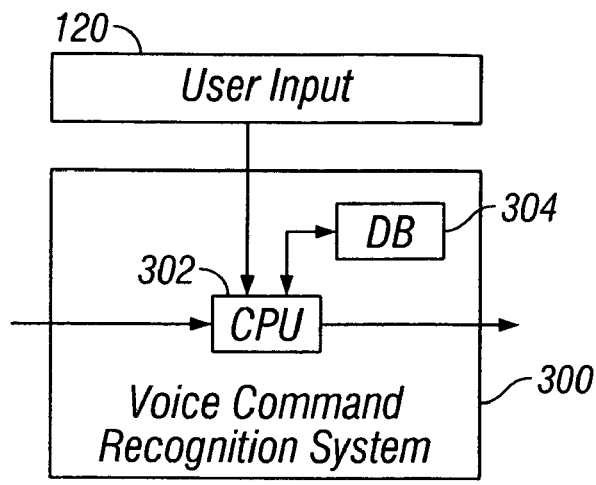
FIG. 6 is a block diagram of a voice command recognition system in accordance with an exemplary embodiment of the present invention.
FIG. 7 is a lookup table of the voice command recognition system of FIG. 6 in accordance with an exemplary embodiment of the present invention.

The association of a voice command with a control command represented by the icon 200 for controlling an operation or parameter of the ultrasound systems 10 and 100 is provided by a voice command recognition system. A block diagram of an exemplary embodiment of a voice command recognition system 300 is shown in FIG. 6. The voice command recognition system 300 includes a processor 302 (e.g., CPU) for receiving an audio signal, such as a voice command from a user, and processing the audio signal to determine the corresponding control command for use in controlling an operation or parameter of the ultrasound systems 10 and 100. The processor 302 also receives information from the user input 120 (e.g., current mode of operation) and accesses a database 304 containing association information for associating a voice command with a control command. It should be noted that the voice command recognition system 300 may be provided separate from or as part of the user input 120 or user interface.

The database 304 contains one or more lookup tables 310 as shown in FIG. 7. It should be noted that the database 304 having the lookup tables 310 contained therein may be stored, for example, in a memory or other storage component, for example, in local memory in the ultrasound systems 10 and 100 or on a server remote from the ultrasound systems 10 and 100. It should also be noted that the association information an may be provided in other forms, such as, for example, as lists in separate files stored within a memory.

As shown in FIG. 7, an exemplary embodiment of a lookup table 310 includes a first column 320, which includes the possible identifiers 212 for one set or row of the matrix in the control portion 180 (e.g., F1 through F4 in FIG. 4). A plurality of mode columns 322 corresponding to the different modes of operation of the ultrasound systems 10 and 100 are provided and include address values corresponding to control commands for each of the modes of operation. Thus, for each identifier entry in the first column 320, a corresponding row includes addresses (e.g., $a_1$ to $a_5$ for five different modes of operation) in the database 304 for the control commands associated with the identifier 212 for each mode of operation. In one exemplary embodiment, the length of the columns and rows is determined based upon the number of identifiers 212 and modes of operation for the ultrasound systems 10 and 100, respectively. It should be noted that separate lookup tables 310 may be provided for each set of identifiers 212 or a single lookup table 310 may be provided for all possible identifiers 212. Additionally, the first column 320 may be modified to include word commands or physical control inputs with the corresponding row entries identifying the addresses in the database 304 for the operations to be performed associated with the word commands or physical control inputs, respectively.

Figure 8:
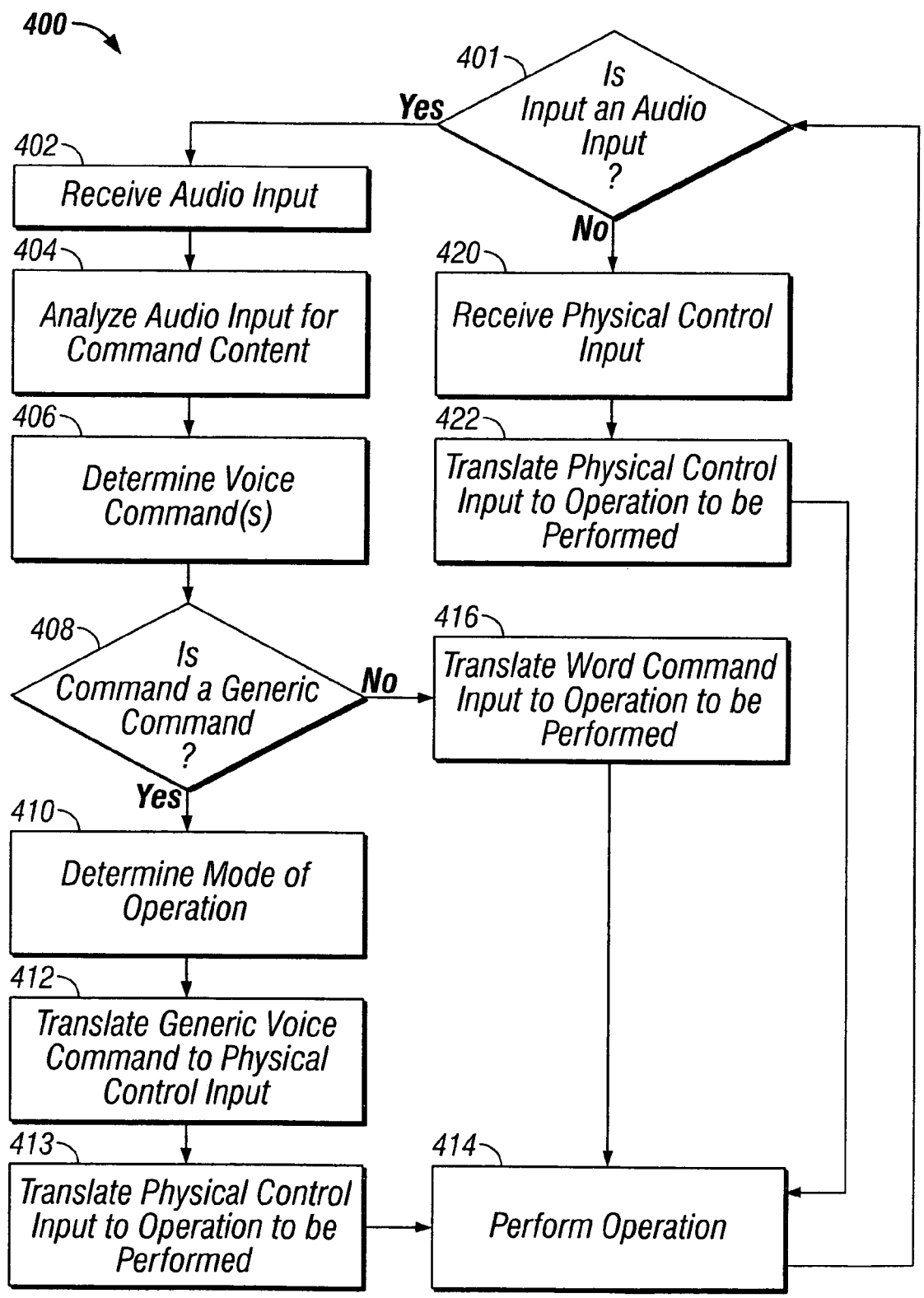
FIG. 8 is a flowchart illustrating a voice recognition process in accordance with an exemplary embodiment of the present invention.

In operation, the voice command recognition system 300 associates a voice command with a control command represented by the icon 200 for controlling an operation or parameter of the ultrasound systems 10 and 100. Specifically, an exemplary embodiment of a voice recognition process 400 performed by the voice command recognition system 300 is shown in FIG. 8. At step 401, a determination is made as to whether the input to the ultrasound system 10 or 100 is an audio input. If the input is an audio input, then at step 402, an audio input (e.g., spoken words from a user) is received. The audio input is then analyzed at step 404 for command content. Based upon the analysis, recognized voice commands are determined at step 406. A determination is then made at step 408 whether the voice command(s) is a generic voice command (i.e., identifier 212). If a determination is made at step 408 that the voice command is a generic voice command, then at step 410 a determination is made as to the mode of operation of the ultrasound systems 10 or 100. At step 412, the generic voice command is translated to a physical control input. For example, using the lookup table 310 (shown in FIG. 7), the address in the database 304 (shown in FIG. 6) of the physical control input (e.g., control command) associated with the identifier 212 for the determined mode of operation is determined. Then, at step 413, the physical control input is translated to the operation to be performed (e.g., determine operation to be performed based upon the physical control input using the lookup table 310). The operation (e.g., adjustment to an operating parameter) is then performed at step 414 based upon the translated generic voice command. Another input is then processed or may be processed in parallel using the voice recognition process 400.

If a determination is made at step 408 that the voice command is not a generic voice command (e.g., command is a word command), then at step 416 the word command is translated to the operation to be performed. For example, a determination is made using the lookup table 310 as to the operation to be performed associated with any word commands (i.e., address in the database 304 (shown in FIG. 6) of the operation to be performed associated with the word command). The operation is then performed at step 414 based upon the determined address. Another input is then processed or may be processed in parallel using the voice recognition process 400.

If a determination is made at step 401 that the input to the ultrasound system 10 or 100 is not an audio input (e.g., input is a physical control input such as a change in a physical dial or switch, or touch on a touch panel) then at step 420 a physical control input (e.g., flipping a switch or rotating a rotary dial) is received. At step 422 the physical control input is translated to the operation to be performed. For example, a determination is made using the lookup table 310 as to the operation to be performed associated with the physical control input (i.e., address in the database 304 (shown in FIG. 6) of the operation to be performed associated with the physical control input). The operation is then performed at step 414 based upon the determined address. Another input is then processed or may be processed in parallel using the voice recognition process 400.

Thus, in operation, user manual action and/or voice commands may be used to control the operation of the ultrasound systems 10 and 100. With respect to voice commands, and for example, using the identifiers 212, the various operations and parameters within each of the modes of operation may be easily controlled. As shown in FIGS. 4 and 5, the screen 150 includes a control portion 180 selectable by a tab 182, with each tab 182 corresponding to a grid layout representing commands and/or parameters for the selected mode of operation. A user, for example, may then speak "Tab" to select the particular tab 182 corresponding to a mode of operation, in this B-mode case, the user would speak "Tab 1", and thereafter, speak a command such as "H1" to operate a particular control within the grid, in this case to turn on/off the Compound feature as determined using the voice recognition process 400. As further examples, the voice command "I4" or "I4 Up" would increase the Line Density setting by one step. The voice command "I4 Down 2" would decrease the Line Density setting by two steps. Further, and as shown in FIG. 5, a voice command such as "Tab 2" could be used to switch from the Carotid tab to the Thyroid tab, causing the screen 150 to display a new set of icons 200 in the control portion 180.

It should be noted that the voice commands for some operations and parameters, such as low use controls, may only be operable using the generic voice commands (i.e., identifiers 212), while voice commands for some operations and parameters, such as high use commands, may be operable using the generic voice command or a word command. For example, a voice command such as "Compound" turns on/off the compounding when in the B-mode of operation as shown in FIG. 4. Alternatively, a voice command such as "H1" may also be used to turn on/off the compounding operation.

To control the physical controls (e.g., rotaries) corresponding to the set of indicators 188, and referring to FIG. 4, a voice command such as "Rotary 1 down 2" decreases the Power Output setting by two steps. It this case, the command would cause the same effect as the physical rotary being turned two clicks to the left. A voice command such as "Push Rotary 1" causes the ultrasound systems 10 and 100 to take the same action as if that physical control was pushed.

Thus, the ease of use of the voice commands of the various embodiments of the present invention provides improved recognition accuracy as a result of the reduced command set size, and also decreases misinterpreted commands due to similar voice commands. Users also are not required to learn a large set of voice commands to control operation of the ultrasound machines 10 and 100, for example, learning all voice commands including low use commands. Users also may view the specific generic commands on the screen 150 as needed and new or additional controls may be associated with a generic voice command (i.e., identifier 212).

While the invention has been described in terms of various specific embodiments, those skilled in the art will recognize that the invention can be practiced with modification within the spirit and scope of the claims.

What is claimed is:

1. A user interface for controlling an ultrasound system, comprising:
    a plurality of selectable elements for controlling operation of the ultrasound system; and
    a plurality of identifiers, each identifier corresponding to one of the plurality of selectable elements and associating control commands with the selectable elements, the plurality of selectable elements operable responsive to voice commands and configured to change based on a mode of operation of the ultrasound system, the plurality of identifiers remaining the same for each of the modes of operation and operable to activate the associated control command of the selectable element based on the mode of operation.

2. A user interface in accordance with claim 1, wherein the plurality of selectable elements are configured for manual selection.

3. A user interface in accordance with claim 1, wherein the plurality of identifiers are voice control identifiers associating the voice commands with the plurality of selectable elements.

4. A user interface in accordance with claim 1, wherein the plurality of selectable elements comprise icons.

5. A user interface in accordance with claim 1, wherein the plurality of selectable elements are configured in a matrix arrangement.

6. A user interface in accordance with claim 1, wherein the plurality of selectable elements comprises a first set of selectable elements and a second set of selectable elements, and wherein the first set of selectable elements is fixed and the second set of selectable elements is configured to change based upon a mode of operation of the ultrasound system.

7. A user interface in accordance with claim 1, wherein the plurality of selectable elements comprise one or more mode selection elements.

8. A user interface in accordance with claim 1, further comprising a voice control input for receiving voice control commands, the identifiers associating the voice control commands with the plurality of selectable elements.

9. A user interface in accordance with claim 8, wherein the voice control commands comprise command words corresponding to one or more of the plurality of selectable elements.

10. A user interface in accordance with claim 1, further comprising a database having stored therein the control commands and a lookup table with addresses associating the selectable elements corresponding to the identifiers with the control commands stored within the database.

11. A user interface in accordance with claim 1, wherein the plurality of identifiers each comprise a single letter and a single number.

12. A voice controlled ultrasound system, comprising:
    a user input providing selection of one or more of a plurality of control commands for controlling the ultrasound system; and
    a voice control input for receiving voice commands corresponding to control commands for controlling the ultrasound system, the control commands provided based on a mode of operation of the ultrasound system and including a plurality of generic voice commands, the plurality of generic voice commands unchanged for each of the modes of operation and corresponding to different control commands based on the mode of operation.

13. A voice controlled ultrasound system in accordance with claim 12, wherein the user input is configured to display voice command identifiers corresponding to each of the plurality of control commands and associating the voice commands with the control commands.

14. A voice controlled ultrasound system in accordance with claim 12, wherein the user input comprises a display for displaying a voice command matrix defining voice command identifiers corresponding to each of the control commands.

15. A voice controlled ultrasound system in accordance with claim 12, wherein the voice control input comprises one of a wired or wireless microphone.

16. A voice controlled ultrasound system in accordance with claim 12, wherein the user input is configured for manual selection of the plurality of control commands.

17. A voice controlled ultrasound system in accordance with claim 12, further comprising a database having stored therein the control commands and a lookup table with addresses associating the voice commands with the control commands stored within the database.

18. A method for controlling an ultrasound system, the method comprising:
    receiving an audio input;
    determining voice commands within the audio input; and
    associating the voice command with a control command to control the operation of the ultrasound system and if the voice command is a generic voice command, determining the mode of operation of the ultrasound system and translating the generic voice command to a corresponding physical control input, the corresponding physical control input different for different modes of operation with the generic voice command unchanged for each of the modes of operation.

19. A method in accordance with claim 18, wherein the voice commands comprise one or more identifiers, and further comprising associating the one or more identifiers with operations for controlling the ultrasound system.

20. A method in accordance with claim 18, further comprising receiving manual user inputs for controlling the ultrasound system.

21. A method in accordance with claim 18, wherein the voice commands comprise word commands corresponding to one or more operations.

22. A method in accordance with claim 18, wherein the associated control commands change based upon a mode of operation of the ultrasound system.

23. A method in accordance with claim 18, wherein the associating comprises accessing a database having stored therein the control commands and a lookup table with addresses for associating the voice commands with the control commands stored within the database.

* * * * *